United States Patent [19]

Lloyd

[11] Patent Number: 4,540,408
[45] Date of Patent: Sep. 10, 1985

[54] APPLICATORS FOR PHARMACOLOGICALLY ACTIVE AGENTS, THEIR PREPARATION AND USE

[75] Inventor: Ronald Lloyd, Sawbridgeworth, United Kingdom

[73] Assignee: Smith and Nephew Associated Companies Limited, United Kingdom

[21] Appl. No.: 373,288

[22] Filed: Apr. 29, 1982

[30] Foreign Application Priority Data

Apr. 30, 1981 [GB] United Kingdom ................ 8113343

[51] Int. Cl.³ ............................................. A61N 7/00
[52] U.S. Cl. .................................... 604/294; 604/290; 604/289
[58] Field of Search ............... 604/892, 893, 894, 895, 604/289, 290, 294, 93

[56] References Cited

U.S. PATENT DOCUMENTS

| | | | |
|---|---|---|---|
| 3,075,527 | 1/1963 | Bechtold | 604/294 |
| 3,625,214 | 12/1971 | Higuchi | 128/260 |
| 3,656,481 | 4/1972 | Ness | 604/294 |
| 3,960,150 | 6/1976 | Hussain et al. | 604/294 |
| 4,036,230 | 7/1977 | Adams | 604/294 |

FOREIGN PATENT DOCUMENTS

| | | | |
|---|---|---|---|
| 609864 | 12/1974 | Switzerland. | |
| 1472306 | 5/1977 | United Kingdom | 604/294 |
| 1485149 | 9/1977 | United Kingdom. | |

Primary Examiner—Richard J. Apley
Assistant Examiner—Gregory Beaucage
Attorney, Agent, or Firm—Jacobs & Jacobs

[57] ABSTRACT

A disposable applicator for placing a pharmacologically active agent in contact with a moist body surface, especially the eye is in the form of an elongate strip disposed at one end of which is a soluble matrix element containing the pharmacologically active agent so that on contact with the moist body surface the matrix element separates from the remainder of the strip. In a preferred form the matrix element is attached to the remainder of the strip by a thin water soluble membrane which rapidly dissolves in body fluid thereby releasing the matrix element to the body surface. Processes for the preparation of the disposable applicators are also described.

9 Claims, 5 Drawing Figures

APPLICATORS FOR PHARMACOLOGICALLY ACTIVE AGENTS, THEIR PREPARATION AND USE

The invention is concerned with applicators for delivering pharmacologically active agents to moist surfaces of the body and more particularly for placing ophthalmic agents onto the eye and processes for their manufacture.

Ophthalmic preparations for the treatment or diagnosis of eye conditions are customarily formulated as sterile aqueous solutions which are put into the eye as drops. Aqueous ophthalmic solutions pose the problems of storage stability of the ophthalmic agent and the maintainence of the solution in sterile condition.

A possible method of overcoming such disadvantages is to employ ophthalmic preparations in solid form which can be inserted into the eye. Inserts of this type in the form of water soluble films have been suggested. However the placing of these films onto the surface of the eye poses a problem of maintainence of sterility and of possible damage or irritation of the eye. British Pat. No. 1,503,427 discloses a re-usable applicator for insertion of such films which is made of a thermoplastic rubber having two flexible jaws for holding the film mounted on a handle at an angle to the jaws to aid insertion. This re-usable applicator has the disadvantages of being cumbersome, requiring sterilisation after each use, requiring the film to be loaded into the jaws and allowing the solid jaws to touch the surface of the eye which might cause damage or irritation.

Certain of the foregoing problems could be eliminated by using an applicator which was disposed of after use. British Patent No. 1,472,306 discloses a disposable applicator comprising a non-liquid absorbing elongate carrier such as a glass rod having at one end an active substance in a very thin, homogenous dry liquid soluble layer. However this applicator suffers from the disadvantage that the rod portion touches the eye and the dose of the active agent delivered into the eye varies with the degree of contact of the rod with the eye.

This problem is overcome in part in an applicator for placing sodium fluorescein in the eye known as "Fluorets". "Fluorets" are in the form of elongated strips having a handle made from paper holding a small strip of absorbent paper containing sodium fluorescein. The sodium fluorescein is applied to the eye by wiping the absorbent paper one or more times across the moist surface of the eye. Unfortunately this applicator gives a somewhat variable dose to the eye and can only be used for water soluble material and the paper can cause irritation to the eye.

Similar devices to 'Fluorets' are described in U.S. Pat. No. 3,075,527 which discloses a medicated applicator of a soft absorbent paper strip impregnated with a dry ophthalmic medicament.

Clearly it would be desirable to ovecome the disadvantages of such known inserts and provide a disposable applicator that can be used to deliver an exact dose of ophthalmic agent to the eye without causing unacceptable irritation and without having contact with the eye with a rigid material. Such a disposable applicator has now been found.

The present invention provides a disposable applicator for placing a pharmacologically active agent in contact with a moist body surface which applicator is in the form of an elongate strip with a pharmacologically active agent disposed at one end thereof characterised in that the pharmacologically active agent is in a soluble matrix element which on contact with the moist body surface separates from the remainder of the strip.

The moist body surfaces with which it is envisaged that the soluble matrix element is to be brought into contact thereby releasing an effective amount of a pharmacologically active agent include the eye, the mucous membranes of the mouth, the nose, the anus and the vagina.

The pharmacologically active agents which are particularly useful for contact with moist body surfaces including the eye include antibacterials as hereinafter described, antibiotics such as oxytetracycline, tetracycline, erythromyin antifungal agents such as griseofulvin, amphotericin B, nystatin and the like which are especially useful in the treatment of fungal infections of the mouth and vagina, antivirals such as idoxuridine, anaesthetics as hereafter described and anti-allergy compounds. Of particular use in vaginal applications may be spermicides such as surfactants which include nonylphenoxypoly(ethyleneoxy)ethanol and the like.

The preferred forms which the applicator may take are as hereinafter described. These are exemplified as applicators for use in the eye. The sklIled worker will recognise which forms of applicator are most appropriate for other moist surfaces and the pharmaceutically active agents they will contain.

In a preferred aspect therefore the present invention provides a disposable applicator for placing an ophthalmic agent onto the eye which applicator is in the form of an elongate strip with an aphthalmic agent disposed at one end thereof characterised in that the ophthalmic agent is in a soluble matrix element which on contact with the moist surface of the eye separates from the remainder of the strip.

When used herein the term "ophthalmic agent" means a substance which can be used for the treatment of eye diseases or disorders or for the diagnosis of eye conditions.

The matrix element is normally a film within which or upon which the ophthalmic agent is distributed.

In a preferred form the applicator has a handle portion, an intermediate flexible portion and a soluble film portion containing the ophthalmic agent. Therefore in another aspect the invention provides an applicator for placing ophthalmic agent into the eye which applicator is in the form of an elongate strip with an ophthalmic agent disposed at one end thereof characterised in that the elongate strip has a handle portion, an intermediate flexible portion and a soluble film portion containing the ophthalmic agent which film portion on contact with the moist surface of the eye separates from the remainder of the strip.

The soluble film portion containing the ophthalmic agent need not be attached to the rest of the elongate strip. However in a preferred form of the applicator the soluble film portion is attached to the rest of the strip by a water activatable separation line. A water activated separation line is a line along which the soluble film portion will separate from the rest of the strip when the soluble film portion of the applicator is applied to an aqueous surface such as the moist surface of the eye. The action of moisture on the separation line should be sufficiently rapid to cause the soluble film portion to separate cleanly and quickly from the rest of the strip. A preferred water activatable separation line is a membrane extending across the strip which is thinner than the film. When the soluble film contacts the moist eye surface the membrane rapidly dissolves so that the soluble film separates from the remainder of the strip. Suitable membrane thicknesses are less than 15 microns and preferably are less than 10 microns. The width of the membrane can be from 0.25 mm to 3 mm and preferably is from 1 mm to 2 mm.

If it is desired to prevent the membrane acting as a flexible hinge which would allow the soluble film portion to 'flap' the membrane may have thicker regions preferably in the form of a regular pattern to improve the membrane stiffness.

To aid the dispersion of the ophthalmic agent into the eye the soluble film portion can have a pattern of thicker and thinner areas. The thinner areas can be thin membranes connecting the thicker areas or apertures. In one preferred form the soluble film portion has a net pattern. Suitable patterns include square grid nets.

In another preferred form the soluble film portion has a pattern of thicker and thinner parallel strips. The pattern of thicker and thinner areas promote the rapid solution of water soluble film by the aqueous eye fluids.

The soluble film portion should have a size and shape which can be accommodated on the surface of the body surface to which it is applied.

Suitable soluble film portions have a maximum surface dimension in any direction of 30 mm. Desirably the soluble film portion is from 3 mm to 20 mm long and from 2 mm to 7.5 mm wide and preferably is from 5 mm to 15 mm long and from 2 mm to 6 mm wide, wherein length is measured from the membrane to the edge of the soluble film portion.

The soluble film portion can have any desired shape. Suitably the film portion can be rectangular including square or circular or elliptical in shape.

Soluble film portions of rectangular shape of size 4 mm×11 mm but preferably 6 mm×5 mm have been found to be satisfactory for insertion onto the eye.

Suitable soluble film portions can have a thickness from 12.5 microns to 125 microns and preferably have a thickness from 20 microns to 50 microns.

Suitable soluble film portions can have a weight of from 10 to 125 gsm and preferably have a weight of 20 to 75 gsm. Suitably the soluble film portion—including ophthalmic agent will have a weight of from 100 micrograms to 30 mg when used on moist body surfaces, for use in the eye the soluble film portion will suitably have a weight of from 200 microgrammes to 3 mg.

The polymer used to make the soluble film portion of the applicator of the invention can be any non toxic water soluble polymer. Suitable water soluble polymers include cellulose derivatives such as alkyl celluloses, for example methyl or ethyl cellulose, hydroxyalkyl celluloses, for example hydroxyethyl cellulose, hydroxypropyl cellulose, alkoxyalkyl celluloses, for example carboxymethyl cellulose, polyacrylates such as water soluble salts of polyacrylic acid such as those with alkali metals, ammonia or other pharmaceutically acceptable nitrogenous bases such as ethanolamine, homopolymers of acrylamide and copolymers of acrylamide with other monomers such as vinyl pyrrolidone, vinyl acetate and ethyl acrylate, polyvinyl alcohol, polyvinyl pyrrolidone, copolymers of methylvinyl ether and maleic anhydride, polyethylene oxide and natural polymers such as gum tragaconth, gelatine, dextran, hydroxylkyl dextrans, dextrin and starch. Preferred water soluble polymers are polyvinyl alcohols. Suitable polyvinyl alcohols have a degree of hydrolysis of from 70 to 93%, more suitably 82% to 92% and preferably have a degree of hydrolysis of from 87% to 89%. Suitable polyvinyl alcohols have a viscosity as a 4% aqueous solution of from 2 centipoises to 25 centipoises.

Favoured polyvinyl alcohols are Gohsenol (Trade Mark) grades GL05 and GM14 made by Nippon Gohsei available from British Traders and Shippers Ltd. Grade GL05 has a degree of hydrolysis of 87% to 89% and a viscosity of 4.8 to 5.8 centipoises as a 4% aqueous solution at 20° C. Grade GM14 has a degree of hydrolysis of 87% to 89% and a viscosity of 21 to 25 centipoises as a 4% aqueous solution at 20° C.

In order to obtain flexible soluble film portions it may be necessary that the water soluble polymer contains up to 20% by weight of plasticiser. Suitable plasticisers include glycerol, ethylene glycol, propylene glycol and polyethylene glycols of low molecular weight.

Suitable ophthalmic agents which can be located in soluble film portions of the applicator of the present invention include anti-infective agents including antibacterials such as silver sulphadiazine, chloramphenicol, aminoglycosides including neomycin sulphate, gentamicin, sodium sulphacetamide, silver nitrate mydriatics and cycloplegics such as atropine sulphate, cyclopentolate hydrochloride, homatrophine hydronbromide hyoscine hyrobromide, phenylephrine hydrochloride and tropicamide, agents useful in the treatment of glaucoma and ocular hypertension, anti-glaucoma agents, which include cholinergic agonists such as physostigmine salicylate, pilocarpine and salts thereof for example pilocarpine nitrate, sympathomimetis such as adrenaline and its salts, for example adrenaline tartrate, adrenaline with guanethidine, β-blockers such as timolol and its salts, for example timolol maleate, other agents suitable for the treatment of glaucoma which include β-methyl noradrenaline, β-methyl adrenaline, triamterene, clonidine, prazosin the dipivoyl esters of adrenaline, noradrenaline, β-methyl adrenaline, β-methyl noradrenaline acetazolamide and methazolamide, anaesthetics such as amethocaine hydrochloride, benoxinate hydrochloride and lignocaine hydrochloride, anti-allergy compounds such as sodium chromoglycate, anti-inflammatory agents including steroids such as betamethasone, cortisone, hydrocortisone, dexamethansone, fluocortolone, prednisolone and triamcinalone and theri pharmacologically acceptable salts such as the acetate or sodium phosphate, and including non-steroidal anti-inflammatory agents such as indomethacin, tolmetin and its salts with alkali metals, for example tolmetin sodium, and stains such as fluoroescein sodium and rose Bengal. The soluble film of the applicator allows both water soluble and insoluble ophthalmic agents to be delivered to the eye.

The amount of pharmacologically active agent present in the soluble film portion will depend on the type of body surface to be treated and the frequency of treatment. Generally the amount of pharmacologically active agent present will be between 1 microgramme and 25 milligrammes.

The ophthalmic agent most suitably will be present in the soluble film portion in an amount which would represent a single dose of the agent. The amount of agent present in a single dose is considered to be that present in one drop of a solution or suspension of the ophthalmic agent which is effective in treatment of the disorder or diagnosis of the eye condition. The size of a drop is typically 50 microliters. Thus depending on the ophthalmic agent used and the dimensions of the soluble film portion, the amount of the ophthalmic agent in the soluble film portion will vary, but is in general from 1 microgramme to 5 milligrams and is preferably from 50 microgrammes to 2.5 milligrams in each soluble film portion.

The weight of pharmacologically active agent present in the soluble film portion will suitably be from 1 to 90% and is preferably from 10 to 40% by weight of the soluble film portion.

In a preferred form the applicator consists of an elongate strip having a handle portion, an intermediate flexible portion and a water soluble polymer film portion containing the ophthalmic agent located at one end of the applicator and connected to the intermediate flexible portion by a thinner membrane line across the strip.

The water soluble film can extend along the whole length of the strip, the film being thicker at the handle and intermediate flexible portions (typically 1.5 to 3 times) than the film at the soluble portion.

The handle portion of the film can be reinforced and stiffened by a suitable paper or plastics material which may be coloured and/or printed to identify the ophthalmic agent in the soluble film portion and to give any other information for example instructions.

The flexible intermediate portion may contact the eye and therefore the polymer film should be sufficiently flexible not to damage or irritate the eye. Suitable water soluble polymers are hereinbefore described.

In a preferred embodiment the applicator consists of a 50 micron thick water soluble polyvinyl alcohol strip reinforced at the handle portion by a paper or plastics material connected by a 2 micron thick membrane line to a 25 micron thick soluble film portion containing the ophthalmic agent.

In another form of the applicator the soluble film portion containing the ophthalmic agent need not be attached to the rest of the elongate strip. The surface of the strip adjacent to the film should be sufficiently soft and flexible to prevent damage or irritation to the eye on contact.

Suitable strips can be made from flexible films and foams of non toxic polymers such as plasticised PVC, polyurethane elastomers, carboxylated butadiene-styrene polymers. A favoured strip is a zinc oxide carboxylated butadiene styrene foam strip. The foam strip can be unsupported in which case the foam can have a thickness of approximately 2500 microns. However it is preferred that the handle portion of the strip be reinforced by a suitable stiff paper or plastics material in which case foam thicknesses of 300 microns to 700 microns are suitable.

The soluble film can be lightly adhered to the flexible end of the strip by means of greasy or oily material. Suitable materials include propylene glycol, glycerol, silicone oil and petroleum jelly.

When the applicator is applied to the moist body surface in a wiping action the soluble film slides off the carrier onto the surface.

Applicators of the invention may be mounted for convenience in handling on a releasable carrier which may extend over part of or the whole of the strip.

The applicator can be conveniently packaged individually or in sets in a bacteria proof pouch and sterilised by irradiation or the like. In use the sterile applicator can be removed by means of the handle portion from the package and the soluble film portion can be applied to the moist surface of the body in a wiping action so that it separates from the remainder of the strip and is left on the body surface. The applicator thereby enables a prescribed dose of drug or diagnostic material to be placed on the body in a simple and sterile manner. The frequency of application will depend on the duration of the drug action or diagnostic period.

Figure 1:
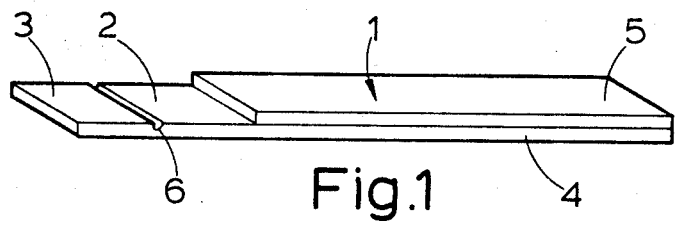
FIG. 1 is a perspective view of an applicator suitable for use in the eye in accordance with the present invention.
Figure 4:
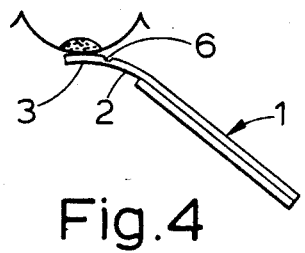
FIG. 4 illustrates the use of the applicators of FIGS. 1 and 2.

In FIG. 1 the applicator is in the form of an elongate strip with a handle portion 1, an intermediate flexible portion 2 and soluble film portion 3 containing the ophthalmic agent. Layer 4 which extends along the whole length of the strip is a water soluble polymer film. Layer 4 as handle portion of the elongate strip is reinforced and stiffened by layer 5 which can be any suitable paper or plastic material. Layer 5 can be coloured and is preferably printed with a code which identifies the ophthalmic agent in soluble film portion 3 of the strip. Layer 4 has a thin membrane 6 between portion 2 and 3 of the elongate strip which is a water activatable separation line so that when the applicator is used as illustrated in FIG. 4, soluble film 3 will separate from the remainder of the strip and be placed in the eye.

Figure 2:
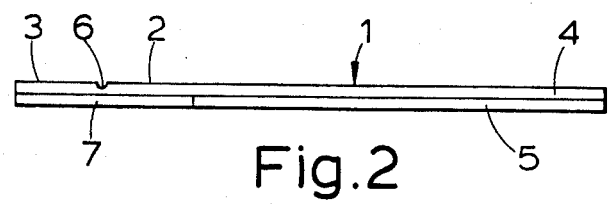
FIG. 2 is a side view of another embodiment of an applicator in accordance with the invention.

FIG. 2 shows a side view of another embodiment of an applicator of the invention which is similar to that of FIG. 1 except that intermediate flexible portion 2 and soluble film 3 of the strip are supported on a release coated carrier 7 which is adjacent to stiffening layer 5 of handle portion 1.

Figure 3:
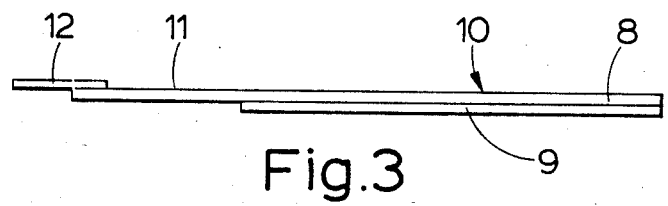
FIG. 3 is a side view of a further embodiment of an applicator in accordance with the invention.
Figure 5:
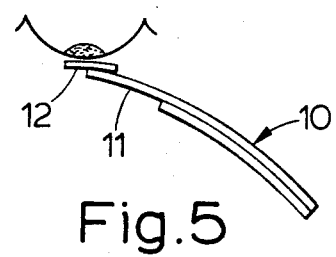
FIG. 5 illustrates the use of the applicator of FIG. 3.

In FIG. 3 the applicator has a layer 8 of a soft material such as a flexible foam which extends along the length of the strip. Layer 8 is reinforced and stiffened by layer 9 to form the handle portion 10. The soluble film portion 12 is a separate piece lightly adhered to layer 8 adjacent to flexible portion 11. When applied to the eye as illustrated in FIG. 5 soluble film portion 12 containing the ophthalmic agent will slide off layer 8 and attach itself to the moist surface of the eye.

In another aspect the present invention provides a process of making an applicator as hereinbefore described which comprises forming an elongate strip with, at one end, a separable soluble film portion containing anpharmacologically active agent.

Most aptly the process will be concerned with making an applicator for delivering an ophthalmic agent to the eye.

A preferred process comprises casting a flexible plastics material as a continuous film or sheet strip onto a carrier and forming a separable soluble film portion at a margin of the continuous strip. Alternatively the separable soluble film portion can be laminated to the film or sheet continuous strip at an end edge margin in a separate operation. Optionally a narrower reinforcing strip of paper or plastics material can be laminated to a margin of the continuous strip to form a handle portion. The reinforcing strip can be laminated to one or both sides of the continuous strip in a separate operation using an adhesive or during the casting operation. The width of the continuous strip can be conveniently the same or a multiple of the desired length of the applicator strip. The continuous strip can then be cut into applicator strips.

In the process of making the preferred form of the applicator of the invention the flexible plastics material is a water soluble polymer as hereinbefore described in relation to the soluble film portion. The water soluble polymer can be cast as an aqueous solution onto a suitable casting paper such as a polyethylene coated paper by means of a coating head. Alternatively the polymer film can be cast as a hot melt for example by extrusion. A water activatable separating line in the continuous film strip can be formed during or after the casting process.

The water activatable separating line is preferably a membrane. A preferred method of forming a membrane in a cast water soluble polymer film is to cast the film as an aqueous solution onto the casting paper using a doctor blade over flat bed coating head in which the doctor blade and/or the flat bed has a raised profile projecting into the gap between the blade and the flat bed.

The raised profile can be of rectangular, triangular, trapezoidal or a pin like shape so as to give a membrane 0.25 to 0.3 mm wide and thickness of less than 15 microns and preferably to give a thickness of less than 10 microns. The raised profile is located to one side of the continuous strip to that resultant soluble film portions will be 5 mm to 25 mm long.

To produce films of different thickness either side of the membrane the coating head can be provided with a multi-sectioned doctor blade which can be set at different gap settings either side of the raised profile. Alternatively different film thicknesses can be produced by using cast solutions of different concentrations which are fed into each side of a spreading head box divided into compartments along the line of the raised profile.

The pharmacologically active agent, for example an ophthalmic agent, can be dispersed or dissolved in the aqueous polymer casting solution prior to use by conventional mixing means. It is preferred that the pharmacologically active agent is only located in the separable soluble film portion of the applicator. It is therefore preferable to isolate the two casting solutions during spreading, for example, by using compartmented spreading head boxes.

The process of forming a continuous strip of a flexible water soluble polymer can be carried out in more than one casting operation if convenient. The continuous strips cast from an aqueous solution can be dried by passage through a heated oven. Polyvinyl alcohol cast continuous strips can be dried at oven temperatures of 40° C. to 90° C.

In a favoured aspect therefore the present invention provides a process for the formation of a disposable applicator for delivering a pharmacologically active agent to a moist body surface which process comprises forming a laminate by (a) forming a film by casting a water soluble polymer from aqueous solution onto a carrier and drying to form a film, (b) casting onto part of this film a second layer of water soluble polymer to form a part of the handle portion and casting onto the other part of the film a layer of water soluble polymer containing a pharmacologically active agent these layers being spaced apart, (c) adhering a reinforcing strip to the handle portion, (d) cutting the resulting layers to form the disposable applicator.

Most aptly the second layer and pharmacologically active agent containing layer are cast simultaneously from a spreading box which has been divided into two compartments of appropriate size.

Preferably the pharmacologically active agent is an ophthalmic agent as hereinbefore defined and the applicator so formed is used to place the ophthalmic agent upon the eye.

In a further aspect of the present invention provides a method of treatment of a moist body surface by applying thereto an effective amount of pharmacologically active agent in a sobuble matrix element which is disposed at one end of a disposable applicator in the form of an elongate strip such that on contact with the moist body surface the soluble matrix element separates from the remainder of the strip.

In a preferred aspect therefore the present invention provides a method of treatment of the eye by applying to the surface thereof an ophthalmic agent in a soluble matrix element which is disposed at one end of a disposable applicator as hereinbefore described.

EXAMPLE 1

Preparation of an Applicator containing an Ophthalmic Agent.

A 10% by weight aqueous solution of polyvinyl alcohol (Gohsenol GM14) was coated onto a polyethylene coated casting paper (Steralease 15 from Sterling Coated Papers Ltd) by a blade over flat bed spreading box (gap setting 75 microns) to give a 7.5 cm wide coating which was dried in an oven at 40° to 50° C. The spreading box was then divided into two compartments approximately 1.5 cm and 6 cm wide using plasticine which extended under the doctor blade (approximately 0.1 mm wide). The dried film on the casting paper was coated (gap setting 200 microns) simultaneously with a 35% by weight aqueous solution of Gohsenol GM14 in the 6 cm wide compartment and with a 15% by weight aqueous soltuion of Gohsenol GM14 containing 1% rose Bengal in the 1.5 cm wide compartment and the coatings dried in an oven at 40° to 50° C. The resultant dried polyvinyl alcohol film had a membrane line 0.1 to 0.2 mm wide and 2 microns thick extending lengthwise and parallel to the edges of the film which divided the film into two parts. The film part containing the rose Bengal was 1.5 cm wide and 25 microns thick. The plain film part was 6 cm wide and had a thickness of approximately 50 microns. A blue paper pressure sensitive coated strip 4.5 cm wide was adhered to the top surface of the plain film part to leave a 1.5 cm wide strip adjacent to the membrane uncovered. The paper strip reinforces and stiffens the film.

The length of film on the casting paper was transversely cut into 4 mm strips and individually packaged in paper peel packs.

The resultant applicator had a stiff handle portion covered with a blue identity paper, an intermediate flexible polyvinyl alcohol portion via a membrane to a thin polyvinyl alcohol film portion containing Rose Bengal.

When the applicator was applied to damp skin to simulate its use in the eye the film portion containing the Rose Bengal instantly separated from the remainder of the strip due to the rapid dissolution of the membrane.

EXAMPLE 2

Preparation of Applicator containing an Ophthalmic Agent.

The following casting solutions are prepared prior to manufacture of the ophthalmic delivery device:

| Casting Solution A. | |
| --- | --- |
| Polyvinyl alcohol (Gohsenol GH17) | 10.0% w/w |
| Distilled water | to 100% w/w |
| Casting Solution B | |
| Polyvinyl alcohol (Gohsenol GH17) | 15.0% w/w |
| Rose Bengal | 1.0% w/w |
| Distilled water | to 100% w/w |
| Casting Solution C | |
| Polyvinyl alcohol (Gohsenol GL05) | 35% w/w |
| Distilled water | to 100% w/w |

Solutions of polyvinyl alcohol are prepared by dispersing the granules of the polymer in cold distilled water with stirring. This dispersion is heated to a temperature of 65° to 70° C. on a steam bath until all the granules have dissolved. The other components are added, and finally the weight of the solution is adjusted to 100 gm by addition of distilled water. The solutions are then allowed to stand overnight for de-areation to take place.

Casting solution A is cast onto a release paper (Steralese 66:02 release paper) using a conventional stainless steel spreading box with a gap of 100 microns. The film is then dried immediately in a hot air oven at 65° to 70° C., taking 4 to 5 minutes to dry.

Casting solutions B and C are spread simultaneously on top of the film cast from solution A. The spreading box used is as before except that the gap width is 200 microns and the box is split into two channels using an aluminium divider 1 mm thick which thereby provides the membrane which allows the soluble film portion, formed by layers of casting Solution A and B to separate from the handle portion of the device. The spread films are dried immediately in a hot air oven as before.

When the films are dry a strip of self adhesive card which may be colour coded or carry printing, is attached to the film cast from solution C such that a gap of 2 mm (approx.) is left between the end of the card and the membrane which connects the handle to the soluble film portion. The multilaminate is then cut the the appropriate size to provide soluble film portions which are for example 6, 8 or 10 mm long and 6 mm wide. These applicators are dessicated over calcium chloride overnight before packing individually into aluminium foil moisture proof envelopes (Sterilite MFEP S4108 available from DRG Ltd).

The packaged applicators may be sterilised by exposure to γ-irradiation at 2.5 Mrad.

In use the sterile applicators are removed from their package, the release paper removed and the soluble film portion placed against the moist surface of the eye. The thin membrane portion dissolves separating the soluble film portion from the handle. The soluble film portion readily dissolves in contact with the moisture in the eye to release the Rose Bengal, a diagnostic agent.

A series of further applications Examples 3- , are prepared in a similar manner to that described in Example 2, the Rose Bengal in Casting Solution B being replaced by sufficient of the pharmacologically active agent to give an effective amount of the pharmacologically active agent in the soluble film portion of each applicator.

| Example | Pharmacologically Active Agent | Weight of Agent/Applicator (microgramme) |
| --- | --- | --- |
| 3 | Chloramphenicol | 250 |
| 4 | Neomycin sulphate | 250 |
| 5 | Gentamycin sulphate | 150 |
| 6 | Silver nitrate | 500 |
| 7 | Tetracycline hydrochloride | 500 |
| 8 | Sulphacetamide sodium | 2000 |
| 9 | Silver sulphadiazine | 2000 |
| 10 | Idoxuridine | 50 |
| 11 | Atropine sulphate | 500 |
| 12 | Cyclopentolate hydrochloride | 250 |
| 13 | Hyosiene hydrobromide | 100 |
| 14 | Tropicamide | 250 |
| 15 | Pilocarpine nitrate | 500 |
| 16 | Adrenaline tartrate | 500 |
| 17 | Timolol maleate | 125 |
| 18 | Trimterene | 100 |
| 19 | Betamethasone sodium phosphate | 50 |
| 20 | Dexamethasone | 50 |
| 21 | Prednisolone sodium phosphate | 50 |
| 22 | Tolmetin sodium | 1000 |
| 23 | Benoxinate hydrochloride | 2000 |
| 24 | Lignocaine hydrochloride | 200 |

Demonstration of Effectiveness

In order to demonstrate the effectiveness of the applicator in delivering an ophthalmic agent onto the eye, applicators were prepared in which tropicamide, a pupil dilator, was suspended in the soluble film portion of the applicator. The applicators were prepared in a manner similar to that described in Example 2.

The concentration of tropicamide in the casting solution was such as to provide a soluble film portion which contained an average 274 microgrammes, 147 microgrammes, 78 microgrammes or 42 microgrammes in each soluble film portion.

The soluble film portion containing the tropicamide was placed into the lower conjunctival sac of one eye of a group of rabbits (White New Zealand/Male). The pupil diameter was measured with a calibrated long focus microscope with a graticule eye-piece at 1 and ½ hours prior to treatment and then at ½, 1, 2, 3, 4, 5 and 6 hours after the application. The mean increase in pupil diameter of the treated eye of each rabbit was measured as compared to the contra-lateral control eye of the rabbit.

Comparative tests were carried out employing tropicamide solutions. In these tests 25 microliters of solution were instilled into the one eye of a group of rabbits (White New Zealand/Male) such that the treated eye received 62.5, 125 or 250 microgrammes of tropicamide. The mean increase in pupil diameter of the treated eye was measured as before.

The results showed:

| Average Weight of Tropicamide in Film Portion (mcg). | Mean Increase in Pupil Diameter (mm) at | | | | | |
| --- | --- | --- | --- | --- | --- | --- |
| | 1 | 2 | 3 | 4 | 5 | 6 (hours) |
| 42 | 2.1 | 2.0 | 2.0 | 1.9 | 1.1 | 1.4 |
| 78 | 2.8 | 2.5 | 2.5 | 2.4 | 2.2 | 2.1 |
| 147 | 3.5 | 3.3 | 3.0 | 2.9 | 2.7 | 2.2 |
| 274 | 3.8 | 3.6 | 3.4 | 3.2 | 3.0 | 2.8 |

| Weight of Tropicamide in | Mean Increase in Pupil Diameter (mm) at |

| Aqueous Solution Dose | 1 | 2 | 3 | 4 | 5 (hours) |
|---|---|---|---|---|---|
| 62.5 | 1.7 | 1.7 | 1.2 | 1.0 | 1.0 |
| 125 | 2.5 | 2.1 | 1.7 | 1.5 | 1.4 |
| 250 | 3.6 | 3.1 | 2.8 | 2.6 | 2.2 |

The results show that the efficacy of tropicamide in dilating pupils when delivered in a soluble film portion is at least as effective as when delivered as conventional drops. The tropicamide when delivered from a water soluble film also has a longer period of effectiveness though the mean maximum effect is achieved after the same time interval, approximately 1 hour.

What we claim is:

1. A disposable applicator for placing a pharmacologically active agent in contact with a moist body surface which applicator is in the form of an elongate strip with a pharmacologically active agent disposed at one end thereof said pharmacologically active agent being in a soluble matrix element which is attached to the rest of the strip by a rapidly soluble water activated membrane along which the soluble matrix element will separate from the remainder of the strip when the soluble matrix element is applied to a moist body surface.

2. A disposable applicator for placing an ophthalmic agent into the eye which applicator is in the form of an elongate strip with an ophthalmic agent disposed at one end thereof said ophthalmic agent being in a water soluble matrix element which is attached to the rest of the strip by a rapidly soluble water activated membrane line along which the soluble matrix element will separate from the remainder of the strip when the soluble matrix element is applied to the moist surface of the eye.

3. A disposable applicator according to claim 2 in which the soluble matrix element is in the form of a soluble film portion comprising a non-toxic water soluble polymer.

4. A disposable applicator according to claim 3 in which the non-toxic water soluble polymer is polyvinyl alcohol.

5. A disposable applicator according to claim 3, in which the soluble film portion is rectangular, including square, in shape.

6. A disposable applicator according to claim 3 in which the soluble film portion is in the shape of a rectangle or square having dimensions of from 3 to 20 mm long, from 2 to 7.5 mm wide and from 12.5 to 125 microns thick.

7. A disposable applicator according to claim 3 in which the soluble film portion has a pattern of thicker and thinner areas.

8. A disposable applicator according to claim 2 in which the weight of ophthalmic agent present in the soluble matrix element is between 1 microgramme to 2.5 milligrams.

9. A disposable applicator according to claim 2 in which the elongate strip has a handle portion, an intermediate flexible portion and a soluble matrix element containing an ophthalmic agent which soluble matrix element is attached to the intermediate flexible portion by a membrane of thickness less than 15 microns which dissolves rapidly in contact with the moist surface of the eye.

* * * * *